US006432668B1

(12) United States Patent
Reinhard et al.

(10) Patent No.: US 6,432,668 B1
(45) Date of Patent: Aug. 13, 2002

(54) POLYNUCLEOTIDES ENCODING HUMAN CYCLIN-DEPENDENT KINASE (HPFTAIRE)

(75) Inventors: Christoph Reinhard, Alameda; David Pot, San Francisco; Altaf Kassam, Oakland; Tasha Marenbach, Berkeley; Lewis T. Williams, Tiburon, all of CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/206,344

(22) Filed: Dec. 7, 1998

Related U.S. Application Data

(60) Provisional application No. 60/068,960, filed on Dec. 30, 1997.

(51) Int. Cl.[7] .......................... C12P 21/06; C12N 9/00; C12N 15/00; C12N 15/09; C12N 15/63
(52) U.S. Cl. .................. 435/69.1; 435/183; 435/320.1; 435/325; 530/350; 536/18.7; 536/22.1; 536/23.1; 536/23.2; 536/23.5; 536/24.3; 536/24.31
(58) Field of Search ............................... 536/18.7, 22.1, 536/23.1, 23.2, 23.5, 24.3, 24.31; 435/320.1, 325, 183, 69.1; 530/350

(56) References Cited

FOREIGN PATENT DOCUMENTS

| DE | 19618985 | 11/1997 |
|----|----------|---------|
| WO | WO 96/28555 | 9/1996 |
| WO | WO 97/25345 | 7/1997 |

OTHER PUBLICATIONS

Bork, Peer. Powers and Pitfalls in Sequence Analysis: The 70% Hurdle. Genome Research 10:398–400, 2000.*
Amino acid and nucleic acid database, Accession #U62391, 1997.*
Amino acid database, Accession #AF033655, 1997.*
Ausuel et al. Short Protocols in Molecular Biology, Second Edition, Unit 16.1:16–4 to 16–9, 1992.*
Besset, V., et al., "The identification and characterization of expression of Pftaire–1, a novel Cdk family member, suggests its function in the mouse testis and nervous system," *Molecular Reproduction and Development* 50:18–29, 1998.
EMBL Database, Accession No. AF033655, Nov. 30, 1997.
Lazarro, M. A., et al. "A novel cdc2–related protein kinase expressed in the nervous system," *Jour. of Neurochemistry* 69(1):348–364, 1997.
Lock, Richard B., et al., "Potentiation of etoposide–induced apoptosis by staurosporine in human tumor cells is associated with events downstream of DNA–protein complex formation," *Cancer Chemother. Pharmacol.* 39:399–409, 1997.

* cited by examiner

*Primary Examiner*—Anthony C. Caputa
*Assistant Examiner*—Alana M. Harris
(74) *Attorney, Agent, or Firm*—Jane E. R. Potter; Kimberlin L. Morley; Robert P. Blackburn

(57) ABSTRACT

A human gene encoding a novel cyclin-dependent kinase termed hPFTAIRE and its expression products can be used to provide reagents and methods for detecting migrating or metastasizing cells. Compositions and methods for treating proliferative disorders and neoplasia are also provided.

8 Claims, No Drawings

US 6,432,668 B1

POLYNUCLEOTIDES ENCODING HUMAN CYCLIN-DEPENDENT KINASE (HPFTAIRE)

This application claims the benefit of provisional application Serial No. 60/068,960 filed Dec. 30, 1997, which is incorporated herein by reference.

TECHNICAL AREA OF THE INVENTION

The invention relates to the area of protein kinases. More particularly, the invention relates to cyclin-dependent protein kinases.

BACKGROUND OF THE INVENTION

The pathways responsible for regulating mitosis and migration and for transducing environmental stress signals in cells have not been fully described. Such proteins can be manipulated, for example, to protect cells against stress due to disease or environmental conditions and to treat disorders involving alterations in mitosis or migration, such as neoplasia. Thus, there is a need in the art for the identification of proteins which are involved in these pathways.

SUMMARY OF THE INVENTION

It is an object of the invention to provide methods and reagents for diagnosing and treating neoplasia, as well as regulating the cell cycle. These and other objects of the invention are provided by one or more of the embodiments described below.

One embodiment of the invention is an isolated protein comprising an amino acid sequence which is at least 94% identical to the amino acid sequence shown in SEQ ID NO:2. Percent identity is determined using a Smith-Waterman homology search algorithm using an affine gap search with a gap open penalty of 12 and a gap extension penalty of 1.

Another embodiment of the invention is an isolated polypeptide comprising at least 218 contiguous amino acids selected from the amino acid sequence shown in SEQ ID NO:2.

Still another embodiment of the invention is a fusion protein comprising a first protein segment and a second protein segment fused to each other by means of a peptide bond. The first protein segment consists of at least 218 contiguous amino acids selected from the amino acid sequence shown in SEQ ID NO:2.

Yet another embodiment of the invention is a cDNA molecule which encodes a protein comprising an amino acid sequence which is at least 94% identical to the amino acid sequence shown in SEQ ID NO:2. Percent identity is determined using a Smith-Waterman homology search algorithm using an affine gap search with a gap open penalty of 12 and a gap extension penalty of 1.

Even another embodiment of the invention is a cDNA molecule which encodes at least 218 contiguous amino acids of SEQ ID NO:2.

A further embodiment of the invention is a cDNA molecule which is at least 85% identical to the nucleotide sequence shown in SEQ ID NO:1. Percent identity is determined using a Smith-Waterman homology search algorithm using an affine gap search with a gap open penalty of 12 and a gap extension penalty of 1.

Another embodiment of the invention is an isolated and purified subgenomic polynucleotide comprising a nucleotide sequence which hybridizes to SEQ ID NO:1 after washing with 0.2×SSC at 65° C. The nucleotide sequence encodes an hPFTAIRE protein having the amino acid sequence of SEQ ID NO:2.

Still another embodiment of the invention is a construct comprising a promoter and a polynucleotide segment encoding at least 218 contiguous amino acids of an hPFTAIRE protein as shown in SEQ ID NO:2. The polynucleotide segment is located downstream from the promoter. Transcription of the polynucleotide segment initiates at the promoter.

Even another embodiment of the invention is a host cell comprising a construct which comprises a promoter and a polynucleotide segment encoding at least 218 contiguous amino acids of an hPFTAIRE protein as shown in SEQ ID NO:2.

Yet another embodiment of the invention is a homologously recombinant cell having incorporated therein a new transcription initiation unit. The new transcription initiation unit comprises (a) an exogenous regulatory sequence, (b) an exogenous exon, and (c) a splice donor site. The new transcription initiation unit is located upstream of a coding sequence of an hPFTAIRE gene. The hPFTAIRE gene comprises the coding sequence shown in SEQ ID NO:1. The exogenous regulatory sequence directs transcription of the coding sequence of the hPFTAIRE gene.

A further embodiment of the invention is a polynucleotide probe comprising at least 12 contiguous nucleotides of SEQ ID NO:1.

Another embodiment of the invention is a method of detecting migrating cells in a body sample of a human. The body sample is assayed for the presence of an expression product of a gene comprising the coding sequence shown in SEQ ID NO:1. The presence of the expression product indicates that the body sample comprises migrating cells.

Still another embodiment of the invention is a method of diagnosing or prognosing neoplasia. Expression of a first hPFTAIRE gene in a first tissue suspected of being neoplastic is compared with expression of a second hPFTAIRE gene in a second tissue which is normal. The second hPFTAIRE gene comprises the coding sequence shown in SEQ ID NO:1. Over-expression of the first hPFTAIRE gene relative to the second hPFTAIRE gene indicates neoplasia in the first tissue.

Even another embodiment of the invention is a method of identifying an agent which alters mitosis. A cell is contacted with a test compound. Expression of an hPFTAIRE gene is measured. The hPFTAIRE gene comprises the coding sequence shown in SEQ ID NO:1. A test compound which increases expression of the hPFTAIRE gene is identified as a potential agent for inducing mitosis, and a test compound which decreases expression of the hPFTAIRE gene is identified as a potential agent for decreasing mitosis.

The present invention thus provides the art with the amino acid sequence and DNA coding sequence of hPFTAIRE, a unique member of the cyclin-dependent kinase family. The invention can be used, inter alia, to treat neoplasia and other proliferative diseases and to detect the presence of migrating cells.

DETAILED DESCRIPTION OF THE PREFERRED EMBODIMENTS

A novel human cyclin-dependent kinase termed hPFTAIRE is a discovery of the present invention. The hPFTAIRE gene is highly expressed in migrating cells, such as metastatic tumor cells and the cells which migrate during gastrulation and nervous system formation. The hPFTAIRE gene is also highly expressed in neural tissue, particularly in the hippocampus, in the retina, in olfactory sensory cells, in spinal motoneurons, and in dorsal root ganglia.

hPFTAIRE expression is required for a cell to undergo a transition from the $G_2$ to M phase of the cell cycle; thus, hPFTAIRE protein is involved in regulating mitosis. In addition, hPFTAIRE may associate with different cyclins which have different functions. For example, hPFTAIRE is expressed in the testis, a location of high meiotic activity, and may be involved in increasing meiotic activity in that organ.

A hPFTAIRE protein comprises the amino acid sequence disclosed in SEQ ID NO:2. The sequence motif which characterizes the cyclin binding domain of the cyclin-dependent kinases (PSTAIRE in cdk2; SEQ ID NO:11) is replaced in hPFTAIRE by the sequence PFTAIRE (SEQ ID NO:5; amino acids 129–135 of SEQ ID NO:2), which indicates that hPFTAIRE has a distinct specificity for its regulatory cyclin subunit. hPFTAIRE has a regulatory phosphorylation site at amino acids 98 and 99.

Various amino acids of hPFTAIRE can be substituted to form hPFTAIRE variants with one or more altered biological activities. For example, the cyclin-dependent kinase activity or cyclin binding domain of hPFTAIRE can be altered, or substitutions can be made which provide an hPFTAIRE protein which cannot be phosphorylated. Such substitutions can provide hPFTAIRE with altered regulation or a particular subset of biological activities as compared to wild type hPFTAIRE. Cyclin binding domains of other cyclin-dependent kinases, such as NRTALRE (SEQ ID NO:6), PISSLRE (SEQ ID NO:7), PITALRE (SEQ ID NO:8), PLSTIRE (SEQ ID NO:9), PISTVRE (SEQ ID NO:10), PSTAIRE (SEQ ID NO:11), and PNQALRE (SEQ ID NO:12), can be substituted for the cyclin binding domain of hPFTAIRE, PFTAIRE (SEQ ID NO:5; amino acids 129–135 of SEQ ID NO:2) in order to change the cyclin binding specificity of hPFTAIRE. Cyclin-dependent kinase activity of hPFTAIRE can be modified, for example, by substituting an asparagine for the aspartic acid at position 227; this substitution results in a "kinase-dead" form of hPFTAIRE.

Various substitutions can be made in order to provide a non-phosphorylatable form of hPFTAIRE. For example, substitution of a histidine or a phenylalanine for the serine at position 99, or substitution of an alanine or a glutamine for the threonine at position 98, render hPFTAIRE non-phosphorylatable. Other substitutions which affect properties of hPFTAIRE will occur to those of skill in the art and can be made to form biologically altered hPFTAIRE variats.

Other amino acid substitutions which do not affect the kinase or cyclin binding activities of hPFTAIRE can occur naturally or can be made in the laboratory, to form biologically active hPFTAIRE variants. Biologically active variants of hPFTAIRE display cyclin-dependent kinase activity.

Guidance in determining which amino acid residues may be substituted, inserted, or deleted without abolishing biological or immunological activity may be found using computer programs well known in the art, such as DNASTAR software. Preferably, amino acid substitutions in biologically active hPFTAIRE variants are conservative amino acid changes, i.e., substitutions of similarly charged or uncharged amino acids. Conservative replacements are those which take place within a family of amino acids which are related in their side chains. Genetically encoded amino acids are generally divided into four families: acidic (aspartate, glutamate); basic (lysine, arginine, histidine); non-polar (alanine, valine, leucine, isoleucine, proline, phenylalanine, methionine, tryptophan); and uncharged polar (glycine, asparagine, glutamine, cystine, serine, threonine, tyrosine). Phenylalanine, tryptophan, and tyrosine are sometimes classified jointly as aromatic amino acids. It is reasonable to expect that an isolated replacement of a leucine with an isoleucine or valine, an aspartate with a glutunate, a threonine with a serine, or a similar replacement of an amino acid with a structurally related amino acid will not have a major effect on the biological properties of the resulting hPFTAIRE molecule, especially if the replacement does not involve an amino acid at a binding site involved in an interaction of hPFTAIRE and another protein, such as a cyclin.

Biologically active hPFTAIRE variants include glycosylated forms, aggregative conjugates with other molecules, and covalent conjugates with unrelated chemical moieties. Biologically active hPFTAIRE variants also include allelic variants, species variants, and muteins. Truncations or deletions of regions which do not affect the cyclin-dependent kinase activity of hPFTAIRE are also biologically active hPFTAIRE variants. Covalent variants can be prepared by linking functionalities to groups which are found in the amino acid chain or at the N- or C-terminal residue, as is known in the art.

Whether an amino acid substitution results in a functional hPFTAIRE protein or polypeptide can readily be determined by assaying its cyclin-dependent kinase activity. Assays for cyclin-dependent kinase activity are taught, for example, in Lock et al., 1997, *Cancer Chemother. Pharmacol.* 39:399–409. Preferred naturally or non-naturally occurring hPFTAIRE variants have amino acid sequences which are at least 94%, 95%, 96%, or 97% identical to amino acid sequences shown in SEQ ID NO:2; more preferably, the molecules are at least 98% or 99% identical. Percent sequence identity is determined using the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* (1981) 2:482–489.

hPFTAIRE polypeptides contain less than full-length hPFTAIRE and comprise at least 218, 225, 250, 275, 300, 325, 330, 350, 375, or 400 or more contiguous amino acids of an hPFTAIRE protein. hPFTAIRE polypeptides can comprise the cyclin binding domain of hPFTAIRE, PFTAIRE (SEQ ID NO:5; amino acids 129–135 of SEQ ID NO:2) or, for example, can be chimeric polypeptides which comprise hPFTIARE amino acid sequences together with cyclin binding domains of other cyclin-dependent kinases, as disclosed above. Polypeptides in which various amino acid substitutions have been made to prevent phosphorylation of hPFTAIRE or to decrease kinase activity of hPFTAIRE can also be constructed.

hPFTAIRE can be isolated from hPFTAIRE-producing human cells, such as brain, pancreas, kidney, heart, ovary, testis, spleen, migrating glial cells or other migrating cell populations, such as cells of a gastrula, using standard biochemical methods. These methods include, but are not limited to, size exclusion chromatography, ammonium sulfate fractionation, ion exchange chromatography, affinity chromatography, crystallization, electrofocusing, and preparative gel electrophoresis. Cell lines, such as Raji, HL-60, or HeLa, are also sources of hPFTAIRE.

An isolated and purified hPFTAIRE protein or polypeptide is separated from other compounds which nornally associate with the hPFTAIRE protein or polypeptide in a cell, such as cyclin or other proteins, carbohydrates, lipids, or subcellular organelles. A preparation of isolated and purified hPFTAIRE proteins or polypeptides is at least 80% pure; preferably, the preparations are 90%, 95%, or 99% pure.

hPFTAIRE proteins and polypeptides can also be produced by recombinant DNA methods or by synthetic chemical methods. For production of recombinant hPFTAIRE proteins or polypeptides, coding sequences selected from the hPFTARE nucleotide sequence shown in SEQ ID NO:1, or variants of that sequence which encode hPFTAIRE protein or biologically active or altered hPFTAIRE variants, can be expressed in prokaryotic or eukaryotic expression systems. Bacterial, yeast, insect, or mammalian expression systems can be used, as is known in the art. Enzymes can be used to generate hPFTAIRE polypeptides by enzymatic proteolysis of full-length hPFTAIRE protein.

Alternatively, synthetic chemical methods, such as solid phase peptide synthesis, can be used to synthesize an hPFTAIRE protein or polypeptide. General means for the production of peptides, analogs or derivatives are outlined in CHEMISTRY AND BIOCHEMISTRY OF AMINO ACIDS, PEPTIDES, AND PROTEINS—A SURVEY OF RECENT DEVELOPMENTS, B. Weinstein, ed. (1983). Moreover, substitution of D-amino acids for the normal L-stereoisomer can be carried out to increase the half-life of an hPFTAIRE molecule. Biologically active hPFTAIRE variants can be similarly produced.

Fusion proteins comprising at least 218, 225, 250, 275, 300, 325, 330, 350, 375, or 400 or more contiguous hPFTAIRE amino acids can also be constructed. hPFTAIRE fusion proteins are useful for generating antibodies which specifically bind to epitopes of hPFTAIRE and for use in various assay systems. For example, hPFTAIRE fusion proteins can be used to identify proteins which interact with hPFTAIRE protein, such as various cyclins, and influence its function. Physical methods, such as protein affinity chromatography, or library-based assays for protein-protein interactions, such as the yeast two-hybrid or phage display systems, can also be used for this purpose. Such methods are well known in the art and can also be used as drug screens.

An hPFTAIRE fusion protein comprises two protein segments fused together by means of a peptide bond. The first protein segment can be N-terminal or C-terminal, as is convenient. The first protein segment consists of at least 218, 225, 250, 275, 300, 325, 330, 350, 375, or 400 or more contiguous amino acids of an hPFTAIRE protein. The amino acids can be selected from the amino acid sequence shown in SEQ ID NO:2 or from a biologically active or altered variant of that sequence, such as those described above. The first protein segment can also be a full-length hPFTAIRE protein or biologically active or altered variant.

The second protein segment can be a full-length protein or a protein fragment or polypeptide. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (BRP), and chloramphenicol acetyltransferase (CAT). Epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex A DNA binding domain (DBD) fusions, GAL4 DNA binding domain fuisions, and herpes simplex virus (HSV) BP16 protein fusions.

hPFTAIRE fusion proteins can be made by covalently linking the first and second protein segments or by standard procedures in the art of molecular biology. Recombinant DNA methods can be used to prepare hPFTAIRE fusion proteins, for example, by making a DNA construct which comprises coding sequences selected from SEQ ID NO:1 in proper reading frame with nucleotides encoding the second protein segment and expressing the DNA construct in a host cell, as is known in the art. Many kits for constructing fusion proteins are available from companies which supply research labs with tools for experiments, including, for example, Promega Corporation (Madison, Wis.), Stratagene (La Jolla, Calif.), Clontech Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Isolated and purified hPFTAIRE proteins, polypeptides, biologically active or altered variants, or fusion proteins can be used as immunogens, to obtain preparations of antibodies which specifically bind to epitopes of an hPFTAIRE protein or biologically active or altered variant. Preferably, hPFTAIRE epitopes are not present in other human proteins. Typically, at least 6, 8, 10, or 12 contiguous amino acids are required to form an hPFTAIRE epitope. However, epitopes which involve non-contiguous amino acids may require more, e.g., at least 15, 25, or 50 amino acids.

Antibodies which specifically bind to epitopes of hPFTAIRE proteins, polypeptides, fusion proteins, or biologically active variants can be used in immunochemical assays, including but not limited to Western blots, ELISAs, radioimmunoassays, immunohistochemical assays, immunoprecipitations, or other immunochemical assays known in the art. Typically, antibodies of the invention provide a detection signal at least 5-, 10-, or 20-fold higher than a detection signal provided with other proteins when used in such immunochemical assays. Preferably, antibodies which specifically bind to hPFTAIRE epitopes do not detect other proteins in immunochemical assays and can immunoprecipitate hPFTAIRE protein or polypeptides from solution.

Epitopes of hPFTAIRE which are particularly antigenic can be selected, for example, by routine screening of hPFTAIRE polypeptides for antigenicity or by applying a theoretical method for selecting antigenic regions of a protein to the amino acid sequence shown in SEQ ID NO:2. Such methods are taught, for example, in Hopp and Wood, *Proc. Natl. Acad. Sci. U.S.A.* 78, 3824–28 (1981), Hopp and Wood, *Mol. Immunol.* 20, 483–89 (1983), and Sutcliffe et al., *Science* 219, 660–66 (1983).

Any type of antibody known in the art can be generated to bind specifically to hPFTAIRE epitopes. For example, preparations of polyclonal and monoclonal antibodies can be made using standard methods which are well known in the art. Similarly, single-chain antibodies can also be prepared. Single-chain antibodies which specifically bind to hPFTAIRE epitopes can be isolated, for example, from single-chain immunoglobulin display libraries, as is known in the art. The library is "panned" against hPFTAIRE amino acid sequences, and a number of single chain antibodies which bind with high-affinity to different epitopes of hPFTAIRE protein can be isolated. Hayashi et al., 1995, *Gene* 160:129–30. Single-chain antibodies can also be constructed using a DNA amplification method, such as the polymerase chain reaction (PCR), using hybridoma cDNA as a template. Thirion et al., 1996, *Eur. J. Cancer Prev.* 5:507–11.

Single-chain antibodies can be mono- or bispecific, and can be bivalent or tetravalent. Construction of tetravalent, bispecific single-chain antibodies is taught, for example, in Coloma and Morrison, 1997, *Nat. Biotechnol.* 15:159–63. Construction of bivalent, bispecific single-chain antibodies is taught inter alia in Mallender and Voss, 1994, *J. Biol. Chem.* 269:199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, *Int. J. Cancer* 61:497–501; Nicholls et al., 1993, *J. Immunol. Meth.* 165:81–91.

Monoclonal and other antibodies can also be "humanized" in order to prevent a patient from mounting an immune response against the antibody when it is used therapeutically. Such antibodies may be sufficiently similar in sequence to human antibodies to be used directly in therapy or may require alteration of a few key residues. Sequence differences between, for example, rodent antibodies and human sequences can be minimized by replacing residues which differ from those in the human sequences, for example, by site directed mutagenesis of individual residues, or by grafing of entire complementarity determining regions. Alternatively, one can produce humanized antibodies using recombinant methods, as described in GB2188638B. Antibodies which specifically bind to hPFTAIRE epitopes can contain antigen binding sites which are either partially or fully humanized, as disclosed in U.S. Pat. No. 5,565,332.

Other types of antibodies can be constructed and used in methods of the invention. For example, chimeric antibodies can be constructed as disclosed, for example, in WO 93/03151. Binding proteins which are derived from immunoglobulins and which are multivalent and multispecific, such as the "diabodies" described in WO 94/13804, can also be prepared.

Antibodies of the invention can be purified by methods well known in the art. For example, antibodies can be affinity purified by passing the antibodies over a column to which an hPFTAIRE protein, polypeptide, biologically active variant, or fusion protein is bound. The bound antibodies can then be eluted from the column, using a buffer with a high salt concentration.

hPFTAIRE-specific binding polypeptides other than antibodies can also be generated. hPFTAIRE-specific binding polypeptides are polypeptides which bind with hPFTAIRE or its variants and which have a measurably higher binding affinity for hPFTAIRE and polypeptide derivatives of hPFTAIRE than for other polypeptides tested for binding. Higher affinity by a factor of 10 is preferred, more preferably a factor of 100. Such polypeptides can be found, for example, using the yeast two-hybrid system.

Antibodies can be used, inter alia, to detect wild-type hPFTAIRE protein in human tissue and fractions thereof. The antibodies can also be used to detect the presence of mutations in the hPFTAIRE gene which result in under- or over-expression of an hPFTAIRE protein or in expression of an hPFTAIRE protein with altered size or electrophoretic mobility. Optionally, antibodies of the invention can be used to block hPFTAIRE cyclin binding sites or to alter effective levels of functional hPFTAIRE protein.

The invention also provides subgenomic polynucleotides which encodes hPFTAIRE proteins, polypeptides, biologically active or altered variants, fusion proteins, and the like. The hPFTAIRE gene is located on chromosome 7q21–22.

hPFTAIRE subgenomic polynucleotides contain less than a whole chromosome 7 and can be double- or single-stranded. Preferably, the polynucleotides are intron-free.

Purified and isolated hPFTAIRE subgenomic polynucleotides can comprise at least 11, 20, 25, 30, 35, 40, 45, 50, 55, 60, 70, 75, 100, 125, 150, 200, 250, or 300, or more contiguous nucleotides selected from the nucleotide sequence shown in SEQ ID NO:1 or its complement. SEQ ID NO:1 is the coding sequence of the hPFTAIRE gene. The complement of the nucleotide sequence shown in SEQ ID NO:1 can be used provide hPFTAIRE antisense oligonucleotides. hPFTAIRE subgenomic polynucleotides also include polynucleotides which encode hPFTAIRE-specific single-chain antibodies, ribozymes, and biologically active or altered hPFTAIRE variants.

Degenerate nucleotide sequences encoding amino acid sequences of hPFTAIRE protein or biologically active hPFTAIRE variants, as well as homologous nucleotide sequences which are at least 65%, 75%, 85%, 90%, 95%, 96%, 97%, 98%, or 99% identical to the nucleotide sequence shown in SEQ ID NO:1, are also hPFTAIRE subgenomic polynucleotides. Percent sequence identity between the nucleotide sequence of SEQ ID NO:1 and a putative homologous or degenerate hPFTAIRE nucleotide sequence is determined using computer programs which employ the Smith-Waterman algorithm, for example as implemented in the MPSRCH program (Oxford Molecular), using an affine gap search with the following parameters: a gap open penalty of 12 and a gap extension penalty of 1.

Nucleotide sequences which hybridize to the coding sequence shown in SEQ ID NO:1 or its complement with at most 1, 2, 3, 4, 5, 10, 15, 20, 25, 30, or 35% basepair mismatches are also hPFTAIRE subgenomic polynucleotides of the invention. For example, using the following wash conditions—2×SSC (0.3 M sodium chloride, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous hPFTAIRE sequences can be identified which contain at most about 25–30% basepair mismatches with SEQ ID NO:1 or its complement. More preferably, homologous nucleic acid strands contain 15–25% basepair mismatches, even more preferably 5–15% basepair mismatches.

It is well known that the $T_m$ of a double-stranded DNA decreases by 1–1.5° C. with every 1% decrease in homology (Bonner et al., *J. Mol. Biol.* 81, 123 (1973). Homologous hPFTAIRE polynucleotides can therefore be identified, for example, by hybridizing a putative homolgous hPFTAIRE polynucleotide with a polynucleotide having the nucleotide sequence of SEQ ID NO:1, comparing the melting temperature of the test hybrid with the melting temperature of a hybrid comprising a polynucleotide having SEQ ID NO:1 and a polynucleotide which is perfectly complementary to SEQ ID NO:1, and calculating the number of basepair mismatches within the test hybrid.

Nucleotide sequences which hybridize to the coding sequence shown in SEQ ID NO:1 or its complement following stringent hybridization and/or wash conditions are also hPFTAIRE subgenomic polynucleotides of the invention. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions, a combination of temperature and salt concentration should be chosen that is approximately 12–20° C. below the calculated $T_m$ of the hybrid under study. The $T_m$ of a hybrid between the hPFTAIRE sequence shown in SEQ ID NO:1 and a polynucleotide sequence which is 65%, 75%, 85%, 90%, 95%, 96%, 97%, 98%, or 99% identical to SEQ ID NO:1 can be calculated, for example, using the equation of Bolton and McCarthy, *Proc. Natl. Acad. Sci. U.S.A.* 48, 1390 (1962):

$$T_m = 81.5° C. - 16.6(\log_{10}[Na^+]) + 0.41(\%G+C) - 0.63(\%formamide) - 600/l),$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Species homologs of hPFTAIRE subgenomic polynucleotides of the invention can also be identified by making suitable probes or primers and screening cDNA expression libraries from other species, such as mice, monkeys, yeast, or bacteria.

hPFTAIRE subgenomic polynucleotides can be isolated and purified free from other nucleotide sequences using standard nucleic acid purification techniques. For example, restriction enzymes and probes can be used to isolate polynucleotide fragments which comprise nucleotide sequences encoding an hPFTAIRE protein or variant. Isolated and purified subgenomic polynucleotides are in preparations which are free or at least 90% free of other molecules.

Complementary DNA (cDNA) molecules which encode hPFTAIRE proteins are also hPFTAIRE subgenomic polynucleotides of the invention. hPFTAIRE cDNA molecules can be made with standard molecular biology techniques, using hPFTAIRE mRNA as a template. hPFTAIRE cDNA molecules can thereafter be replicated using molecular biology techniques known in the art and disclosed in manuals such as Sambrook et al., 1989. An amplification technique, such as the polymerase chain reaction (PCR), can be used to obtain additional copies of subgenomic polynucleotides of the invention, using either human genomic DNA or cDNA as a template.

Alternatively, synthetic chemistry techniques can be used to synthesize hPFTAIRE subgenomic polynucleotide molecules of the invention. The degeneracy of the genetic code allows alternate nucleotide sequences to be synthesized which will encode an hPFTAIRE protein having the amino acid sequence shown in SEQ ID NO:2 or a biologically active variant of that sequence. All such nucleotide sequences are within the scope of the present invention.

The invention also provides polynucleotide probes which can be used to detect hPFTAIRE sequences, for example, in hybridization protocols such as Northern or Southern blotting or in situ hybridization. Polynucleotide probes of the invention comprise at least 12, 13, 14, 15, 16, 17, 18, 19, 20, 30, or 40 or more contiguous nucleotides selected from SEQ ID NO:1. Polynucleotide probes of the invention can comprise a detectable label, such as a radioisotopic, fluorescent, enzymatic, or chemiluminescent label.

Purified and isolated hPFTAIRE subgenomic polynucleotides can be used as primers to obtain additional copies of the polynucleotides or as probes for identifying wild-type and mutant hPFTAIRE coding sequences. hPFTAIRE subgenomic polynucleotides can also be used to express hPFTAIRE mRNA, protein, polypeptides, fusion proteins and the like and to generate hPFTAIRE antisense oligonucleotides and ribozymes.

An hPFTAIRE subgenomic polynucleotide comprising hPFTAIRE coding sequences can be used in a construct, such as a DNA or RNA construct. The construct can be a vector and can be used to transfer an hPFTAIRE subgenomic polynucleotide into a cell, for example, for propagation of the subgenomic polynucleotide. hPFTAIRE constructs can be linear or circular molecules. They can be on autonomously replicating molecules or on molecules without replication sequences. They can be regulated by their own or by other regulatory sequences, as are known in the art.

An hPFTAIRE construct can be an expression construct which comprises a promoter which is functional in a selected host cell. The skilled artisan can readily select an appropriate promoter from the large number of cell type-specific promoters known and used in the art. The expression construct can also contain a transcription terminator which is functional in the host cell. The expression construct comprises a polynucleotide segment which encodes, for example, all or a portion of an hPFTAIRE protein, variant, fusion protein, antibody, or ribozyme. The polynucleotide segment is located downstream from the promoter. Transcription of the polynucleotide segment initiates at the promoter.

A recombinant host cell comprising an hPFTAIRE construct can be constructed and used to express all or a portion of an hPFTAIRE protein. Recombinant host cells comprising hPFTAIRE expression constructs can be prokaryotic or eukaryotic. A variety of host cells are available for use in bacterial, yeast, insect, and human expression systems and can be used to express or to propagate hPFTAIRE expression constructs (see below). Constructs can be introduced into host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and calcium phosphate-mediated transfection.

Bacterial systems for expressing hPFTAIRE expression constructs include those described in Chang et al., *Nature* (1978) 275: 615, Goeddel et al., *Nature* (1979) 281: 544, Goeddel et al., *Nucleic Acids Res.* (1980) 8: 4057, EP 36,776, U.S. Pat. No. 4,551,433, deBoer et al., *Proc. Natl. Acad. Sci. USA* (1983) 80: 21–25, and Siebenlist et al., *Cell* (1980) 20: 269.

Expression systems in yeast include those described in Hinnen et al., *Proc. Natl. Acad. Sci. USA* (1978) 75: 1929; Ito et al., *J. Bacteriol.* (1983) 153: 163; Kurtz et al., *Mol. Cell. Biol.* (1986) 6:142; Kunze et al., *J. Basic Microbiol.* (1985) 25: 141; Gleeson et al., *J. Gen. Microbiol.* (1986) 132: 3459, Roggenkamp et al., *Mol. Gen. Genet.* (1986) 202:302) Das et al., *J. Bacteriol.* (1984) 158: 1165; De Louvencourt et al., *J. Bacteriol.* (1983) 154: 737, Van den Berg et al., *Bio/Technology* (1990) 8: 135; Kunze et al., *J. Basic Microbiol.* (1985) 25: 141; Cregg et al., *Mol. Cell. Biol.* (1985) 5: 3376, U.S. Pat. No. 4,837,148, U.S. Pat. No. 4,929,555; Beach and Nurse, *Nature* (1981) 300: 706; Davidow et al., *Curr. Genet.* (1985) 10: 380, Gaillardin et al., *Curr. Genet.* (1985) 10: 49, Ballance et al., *Biochem. Biophys. Res. Commun.* (1983) 112: 284–289; Tilburn et al., *Gene* (1983) 26: 205–221, Yelton et al., *Proc. Natl. Acad Sci. USA* (1984) 81:1470–1474, Kelly and Hynes, *EMBO J.* (1985) 4: 475479; EP 244,234, and WO 91/00357.

Expression of hPFTAIRE expression constructs in insects can be carried out as described in U.S. Pat. No. 4,745,051, Friesen et al. (1986) "The Regulation of Baculovirus Gene Expression" in: THE MOLECULAR BIOLOGY OF BACULOVIRUSES (W. Doerfler, ed.), EP 127,839, EP 155,476, and Vlak et al., *J. Gen. Virol.* (1988) 69: 765–776, Miller et al., *Ann.*

Rev. Microbiol. (1988) 42: 177, Carbonell et al., *Gene* (1988) 73: 409, Maeda et al., *Nature* (1985) 315: 592–594, Lebacq-Verheyden et al., *Mol. Cell. Biol.* (1988) 8: 3129; Smith et al., *Proc. Natl. Acad Sci. USA* (1985) 82: 8404, Miyajima et al., *Gene* (1987)58: 273; and Martin et al., *DNA* (1988) 7.99. Numerous baculoviral strains and variants and corresponding permissive insect host cells from hosts are described in Luckow et al., *Bio/Technology* (1988) 6: 47–55, Miller et al., in GENCENIC ENGINEERING (Setlow, J. K. et al. eds.), Vol. 8 (Plenum Publishing, 1986), pp. 277–279, and Maeda et al., *Nature*, (1985) 315: 592–594.

Mammalian expression of hPFTAIRE expression constructs can be achieved as described in Dijkema et al., *EMBO J.* (1985) 4: 761, Gorman et al., *Proc. Natl. Acad. Sci. USA* (1982b) 79: 6777, Boshart et al., *Cell* (1985) 41: 521 and U.S. Pat. No. 4,399,216. Other features of mammalian expression of hPFTAIRE expression constructs can be facilitated as described in Ham and Wallace, *Meth. Enz.* (1979) 58: 44, Barnes and Sato, *Anal. Biochem.* (1980) 102: 255, U.S. Pat. No. 4,767,704, U.S. Pat. No. 4,657,866, U.S. Pat. No. 4,927,762, U.S. Pat. No. 4,560,655, WO 90/103430, WO 87/00195, and U.S. Pat. No. RE 30,985.

Subgenomic polynucleotides of the invention can also be used in gene delivery vehicles, for the purpose of delivering the hPFTAIRE to a cell, preferably a eukaryotic cell. According to the present invention, a gene delivery vehicle can be, for example, naked plasmid DNA, a viral expression vector comprising an hPFTAIRE subgenomic polynucleotide, or an hPFTAIRE subgenomic polynucleotide in conjunction with a liposome or a condensing agent.

In one embodiment of the invention, the gene delivery vehicle comprises a promoter and an hPFTAIRE subgenomic polynucleotide. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter.

An hPFTAIRE gene delivery vehicle can comprise viral sequences such as a viral origin of replication or packaging signal. These viral sequences can be selected from viruses such as astrovirus, coronavirus, orthomyxovirus, papovavirus, paramyxovirus, parvovirus, picomavirus, poxvirus, retrovirus, togavirus or adenovirus. In a preferred embodiment, the hPFTAIRE gene delivery vehicle is a recombinant retroviral vector. Recombinant retroviruses and various uses thereof have been described in numerous references including, for example, Mann et al., *Cell* 33:153, 1983, Cane and Mulligan, *Proc. Nat'l. Acad. Sci. USA* 81:6349, 1984, Miller et al., *Human Gene Therapy* 1:5–14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, *Cancer Res.* 53:3860–3864, 1993; Vile and Hart, *Cancer Res.* 53:962–967, 1993; Ram et al., *Cancer Res.* 53:83–88, 1993; Takamiya et al., *J. Neurosci. Res.* 33:493–503, 1992; Baba et al., *J. Neurosurg.* 79:729–735, 1993 (U.S. Pat. No. 4,777,127, GB 2,200,651, EP 0,345,242 and WO91/02805). Particularly preferred retroviruses are derived from retroviruses which include avian leukosis virus (ATCC Nos. VR-535 and VR-247), bovine leukemia virus (VR-1315), murine leukemia virus (MLV), mink-cell focus-inducing virus (Koch et al., *J. Vir.* 49:828, 1984; and Oliff et al., *J. Vir.* 48:542, 1983), murine sarcoma virus (ATCC Nos. VR-844, 45010 and 45016), reticuloendotheliosis virus (ATCC Nos VR-994, VR-770 and 45011), Rous sarcoma virus, Mason-Pfizer monkey virus, baboon endogenous virus, endogenous feline retrovirus (e.g., RD114), and mouse or rat gL30 sequences used as a retroviral vector. Particularly preferred strains of MLV from which recombinant retroviruses can be generated include 4070A and 1504A (Hartley and Rowe, *J. Vir.* 19:19, 1976), Abelson (ATCC No. VR-999), Friend (ATCC No. VR-245), Graffi (Ru et al., *J. Vir.* 67:4722, 1993; and Yantchev *Neoplasma* 26:397, 1979), Gross (ATCC No. VR-590), Kirsten (Albino et al., *J. Exp. Med.* 164:1710, 1986), Harvey sarcoma virus (Manly et al., *J. Vir.* 62:3540, 1988; and Albino et al., *J. Exp. Med.* 164:1710, 1986) and Rauscher (ATCC No. VR-998), and Moloney MLV (ATCC No. VR-190). A particularly preferred non-mouse retrovirus is Rous sarcoma virus. Preferred Rous sarcoma viruses include Bratislava (Manly et al., *J. Vir.* 62:3540, 1988; and Albino et al., *J. Exp. Med.* 164:1710, 1986), Bryan high titer (e.g., ATCC Nos. VR-334, VR-657, VR-726, VR-659, and VR-728), Bryan standard (ATCC No. VR-140), Carr-Zilber (Adgighitov et al., *Neoplasma* 27:159, 1980), Engelbreth-Holm (Laurent et al., *Biochem Biophys Acta* 908:241, 1987), Harris, Prague (e.g., ATCC Nos. VR-772, and 45033), and Schmidt-Ruppin (e.g. ATCC Nos. VR-724, VR-725, VR-354) viruses.

Any of the above retroviruses can be readily utilized in order to assemble or construct retroviral hPFTAIRE gene delivery vehicles given the disclosure provided herein and standard recombinant techniques (e.g., Sambrook et al., *Molecular Cloning: A Laboratory Manual*, 2d ed., Cold Spring Harbor Laboratory Press, 1989, and Kunkle, *PROC. NATL. ACAD. SCI. U.S.A.* 82:488, 1985) known in the art. Portions of retroviral hPFTAIRE expression vectors can be derived from different retroviruses. For example, retrovector LTRs can be derived from a murine sarcoma virus, a tRNA binding site from a Rous sarcoma virus, a packaging signal from a murine leukemia virus, and an origin of second strand synthesis from an avian leukosis virus. These recombinant retroviral vectors can be used to generate transduction competent retroviral vector particles by introducing them into appropriate packaging cell lines (see Ser. No. 07/800, 921, filed Nov. 29, 1991). Recombinant retroviruses can be produced which direct the site-specific integration of the recombinant retroviral genome into specific regions of the host cell DNA. Such site-specific integration can be mediated by a chimeric integrase incorporated into the retroviral particle (see Ser. No. 08/445,466 filed May 22, 1995). It is preferable that the recombinant viral gene delivery vehicle is a replication-defective recombinant virus.

Packaging cell lines suitable for use with the above-described retroviral gene delivery vehicles can be readily prepared (see Ser. No. 08/240,030, filed May 9, 1994; see also WO 92/05266) and used to create producer cell lines (also termed vector cell lines or "VCLs") for production of recombinant viral particles. In particularly preferred embodiments of the present invention, packaging cell lines are made from human (e.g., HT1080 cells) or mink parent cell lines, thereby allowing production of recombinant retroviral gene delivery vehicles which are capable of surviving inactivation in human serum. The construction of recombinant retroviral gene delivery vehicles is described in detail in WO 91/02805. These recombinant retroviral gene delivery vehicles can be used to generate transduction competent retroviral particles by introducing them into appropriate packaging cell lines (see Ser. No. 07/800,921). Similarly, adenovirus gene delivery vehicles can also be readily prepared and utilized given the disclosure provided herein (see also Berkner, *Biotechniques* 6:616–627, 1988, and Rosenfeld et al., *Science* 252:431–434, 1991, WO 93/07283, WO 93/06223, and WO 93/07282).

An hPFTAIRE gene delivery vehicle can also be a recombinant adenoviral gene delivery vehicle. Such vehicles can be readily prepared and utilized given the disclosure provided herein (see Berkner, *Biotechniques* 6:616, 1988, and Rosenfeld et al., *Science* 252:431, 1991, WO 93/07283, WO 93/06223, and WO 93/07282). Adeno-assciated viral hPFTAIRE gene delivery vehicles can also be constructed and used to deliver hPFTAIRE amino acids or nucleotides. The use of adeno-associated viral gene delivery vehicles in vitro is described in Chatterjee et al., *Science* 258: 1485–1488 (1992), Walsh et al., *Proc. Nat'l. Acad. Sci.* 89: 7257–7261 (1992), Walsh et al., *J. Clin. Invest.* 94: 1440–1448 (1994), Flotte et al., *J. Biol. Chem.* 268: 3781–3790 (1993), Ponnazhagan et al., *J. Exp. Med.* 179: 733–738 (1994), Miller et al., *Proc. Nat'l Acad. Sci.* 91: 10183–10187 (1994), Einerhand et al., *Gene Ther.* 2: 336–343 (1995), Luo et al., *Exp. Hematol.* 23: 1261–1267 (1995), and Zhou et al., *Gene Therapy* 3: 223–229 (1996). In vivo use of these vehicles is described in Flotte et al, *Proc. Nat'l Acad. Sci.* 90: 10613–10617 (1993), and Kaplitt et al., *Nature Genet.* 8:148–153 (1994).

In another embodiment of the invention, an hPFTAIRE gene delivery vehicle is derived from a togavirus. Preferred togaviruses include alphaviruses, in particular those described in U.S. Ser. No. 08/405,627, filed Mar. 15, 1995, WO 95/07994. Alpha viruses, including Sindbis and ELVS viruses can be gene delivery vehicles for hPFTAIRE polynucleotides. Alpha viruses are described in WO 94/21792, WO 92/10578 and WO 95/07994. Several different alphavirus gene delivery vehicle systems can be constructed and used to deliver hPFTAIRE subgenomic polynucleotides to a cell according to the present invention. Representative examples of such systems include those described in U.S. Pat Nos. 5,091,309 and 5,217,879. Particularly preferred alphavirus gene delivery vehicles for use in the present invention include those which are described in WO 95/07994, and U.S. Ser. No. 08/405,627.

Preferably, the recombinant viral vehicle is a recombinant alphavirus viral vehicle based on a Sindbis virus. Sindbis constructs, as well as numerous similar constructs, can be readily prepared essentially as described in U.S. Ser. No. 08/198,450. Sindbis viral gene delivery vehicles typically comprise a 5' sequence capable of initiating Sindbis virus transcription, a nucleotide sequence encoding Sindbis nonstructural proteins, a viral junction region inactivated so as to prevent subgenomic fragment transcription, and a Sindbis RNA polymerase recognition sequence. Optionally, the viral junction region can be modified so that subgenomic polynucleotide transcription is reduced, increased, or maintained. As will be appreciated by those in the art, corresponding regions from other alphaviruses can be used in place of those described above.

The viral junction region of an alphavirus-derived gene delivery vehicle can comprise a first viral junction region which has been inactivated in order to prevent transcription of the subgenomic polynucleotide and a second viral junction region which has been modified such that subgenomic polynucleotide transcription is reduced. An alphavirus-derived vehicle can also include a 5' promoter capable of initiating synthesis of viral RNA from cDNA and a 3' sequence which controls transcription termination.

Other recombinant togaviral gene delivery vehicles which can be utilized in the present invention include those derived from Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309 and 5,217,879 and in WO 92/10578. The Sindbis vehicles described above, as well as numerous similar constructs, can be readily prepared essentially as described in U.S. Ser. No. 08/198,450.

Other viral gene delivery vehicles suitable for use in the present invention include, for example, those derived from poliovirus (Evans et al., *Nature* 339:385, 1989, and Sabin et al., *J. Biol. Standardization* 1:115, 1973) (ATCC VR-58); rhinovirus (Arnold et al., *J. Cell. Biochem.* L401, 1990) (ATCC VR-1 110); pox viruses, such as canary pox virus or vaccinia virus (Fisher-Hoch et al., *PROC. NATL. ACAD. SCI. U.S.A.* 86:317, 1989; Flexner et al., *Ann. N.Y. Acad. Sci.* 569:86, 1989; Flexner et al., *Vaccine* 8:17, 1990; U.S. Pat. No. 4,603,112 and U.S. Pat. No. 4,769,330; WO 89/01973) (ATCC VR-111; ATCC VR-2010); SV40 (Mulligan et al., *Nature* 277:108, 1979) (ATCC VR-305), (Madzak et al., *J. Gen. Vir.* 73:1533, 1992); influenza virus (Luytjes et al., *Cell* 59:1107, 1989; McMicheal et al., *The New England Jounal of Medicine* 309:13, 1983; and Yap et al., *Nature* 273:238, 1978) (ATCC VR-797); parvovirus such as adeno-associated virus (Samulski et al., *J. Vir.* 63:3822, 1989, and Mendelson et al., *Virology* 166:154, 1988) (ATCC VR-645); herpes simplex virus (Kit et al., *Adv. Exp. Med. Biol.* 215:219, 1989) (ATCC VR-977; ATCC VR-260); *Nature* 277:108, 1979); human immunodeficiency virus (EPO 386, 882, Buchschacher et al., *J. Vir.* 66:2731, 1992); measles virus (EPO 440,219) (ATCC VR-24); A (ATCC VR-67; ATCC VR-1247), Aura (ATCC VR-368), Bebaru virus (ATCC VR-600; ATCC VR-1240), Cabassou (ATCC VR-922), Chikungunya virus (ATCC VR-64; ATCC VR-1241), Fort Morgan (ATCC VR-924), Getah virus (ATCC VR-369; ATCC VR-1243), Kyzylagach (ATCC VR-927), Mayaro (ATCC VR-66), Mucambo virus (ATCC VR-580; ATCC VR-1244), Ndumu (ATCC VR-371), Pixuna virus (ATCC VR-372; ATCC VR-1245), Tonate (ATCC VR-925), Triniti (ATCC VR-469), Una (ATCC VR-374), Whataroa (ATCC VR-926), Y-62–33 (ATCC VR-375), O'Nyong virus, Eastern encephalitis virus (ATCC VR-65; ATCC VR-1242), Western encephalitis virus (ATCC VR-70; ATCC VR-1251; ATCC VR-622; ATCC VR-1252), and coronavirus (Hamre et al., *Proc. Soc. Exp. Biol. Med.* 121:190, 1966) (ATCC VR-740).

An hPFTAIRE subgenomic polynucleotide of the invention can also be combined with a condensing agent to form a gene delivery vehicle. In a preferred embodiment, the condensing agent is a polycation, such as polylysine, polyarginine, polyornithine, protamine, spermine, spermidine, and putrescine. Many suitable methods for making such linkages are known in the art (see, for example, Ser. No. 08/366,787, filed Dec. 30, 1994).

In an alternative embodiment, an hPFTAIRE subgenomic polynucleotide is associated with a liposome to form a gene delivery vehicle. Liposomes are small, lipid vesicles comprised of an aqueous compartment enclosed by a lipid bilayer, typically spherical or slightly elongated structures several hundred Angstroms in diameter. Under appropriate conditions, a liposome can fuse with the plasma membrane of a cell or with the membrane of an endocytic vesicle within a cell which has internalized the liposome, thereby releasing its contents into the cytoplasm. Prior to interaction with the surface of a cell, however, the liposome membrane acts as a relatively impermeable barrier which sequesters and protects its contents, for example, from degradative enzymes. Additionally, because a liposome is a synthetic structure, specially designed liposomes can be produced which incorporate desirable features. See Stryer, *Biochemistry*, pp.236–240, 1975 (W. H. Freeman, San Francisco, Calif.); Szoka et al., *Biochim. Biophys. Acta* 600:1, 1980; Bayer et al., *Biochim. Biophys. Acta.* 550:464, 1979; Rivnay et al., *Meth. Enzymol.* 149:119, 1987; Wang et al., *Proc. Natl. Acad. Sci. U.S.A.* 84: 7851, 1987, Plant et al., *Anal. Biochem.* 176:420, 1989, and U.S. Pat. No. 4,762,915. Liposomes can encapsulate a variety of nucleic acid molecules including DNA, RNA, plasmids, and expression constructs comprising hPFTAIRE subgenomic polynucleotides such those disclosed in the present invention.

Liposomal preparations for use in the present invention include cationic (positively charged), anionic (negatively charged) and neutral preparations. Cationic liposomes have been shown to mediate intracellular delivery of plasmid DNA (Felgner et al., *Proc. Natl. Acad. Sci. USA* 84:7413–7416, 1987), mRNA (Malone et al., *Proc. Natl. Acad. Sci. USA* 86:6077–6081, 1989), and purified transcription factors (Debs et al., *J. Biol. Chem*. 265:10189–10192, 1990), in functional form. Cationic liposomes are readily available. For example, N[1-2,3-dioleyloxy)propyl]-N,N,N-triethylammonium (DOTMA) liposomes are available under the trademark Lipofectin, from S' GIBCO BRL, Grand Island, N.Y. See also Felgner et al., *Proc. Natl. Acad. Sci. USA* 91: 5148–5152.87, 1994. Other commercially available liposomes include Transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* 75:4194–4198, 1978; and WO 90/11092 for descriptions of the synthesis of DOTAP (1,2-bis(oleoyloxy)-3-(trimethylammonio)propane) liposomes.

Similarly, anionic and neutral liposomes are readily available, for example from Avanti Polar Lipids (Birfmingmm, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., METHODS OF IMMUNOLOGY (1983), Vol. 101, pp. 512–527; Szoka et al., *Proc. Natl. Acad. Sci. USA* 87:3410–3414, 1990; Papahadjopoulos et al., *Biochim. Biophys. Acta* 394:483, 1975; Wilson et al., *Cell* 17:77, 1979; Deamer and Bangham, *Biochim. Biophys. Acta* 443:629, 1976; Ostro et al., *Biochem. Biophys. Res. Commun*. 76:836, 1977; Fraley et al., *Proc. Natl. Acad. Sci. USA* 76:3348, 1979; Enoch and Strittmatter, *Proc. Natl. Acad. Sci. USA* 76:145, 1979; Fraley et al., *J. Biol. Chem*. 255:10431, 1980; Szoka and Papahadjopoulos, *Proc. Natl. Acad. Sci. USA* 75:145, 1979; and Schaefer-Ridder et al., *Science* 215:166, 1982.

In addition, lipoproteins can be included with an hPFTAIRE subgenomic polynucleotide for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of polynucleotides to cells expressing lipoprotein receptors. Preferably, if lipoproteins are included with a polynucleotide, no other targeting ligand is included in the composition.

In another embodiment, naked hPFTAIRE subgenomic polynucleotide molecules are used as gene delivery vehicles, as described in WO 90/11092 and U.S. Pat. No. 5,580,859. Such gene delivery vehicles can be either hPFTAIRE DNA or RNA and, in certain embodiments, are linked to killed adenovirus. Curiel et al., *Hum. Gene. Ther*. 3:147–154, 1992. Other suitable vehicles include DNA-ligand (Wu et al., *J. Biol. Chem*. 264:16985–16987, 1989), lipid-DNA combinations (Felgner et al., *Proc. Natl. Acad. Sci. USA* 84:7413 7417, 1989), liposomes (Wang et al., *Proc. Natl. Acad. Sci*. 84:7851–7855, 1987) and microprojectiles (Williams et al., *Proc. Natl. Acad. Sci*. 88:2726–2730, 1991).

One can increase the efficiency of naked hPFTAIRE subgenomic polynucleotide uptake into cells by coating the polynucleotides onto biodegradable latex beads. This approach takes advantage of the observation that latex beads, when incubated with cells in culture, are efficiently transported and concentrated in the perinuclear region of the cells. The beads will then be transported into cells when injected into muscle. hPFTAIRE subgenomic polynucleotide-coated latex beads will be efficiently transported into cells after endocytosis is initiated by the latex beads and thus increase gene transfer and expression efficiency. This method can be improved further by treating the beads to increase their hydrophobicity, thereby facilitating the disruption of the endosome and release of hPFTAIRE subgenomic polynucleotides into the cytoplasm.

The present invention provides a method of detecting migrating cells in a human body sample. The basis for this method is the discovery that hPFTAIRE mRNA is highly expressed in cells which are undergoing migration, such as cells of the developing nervous system, cells involved in gastrulation, and metastasizing cells.

In one embodiment, the body sample is assayed for the presence of an expression product of the hPFTAIRE gene, such as hPFTAIRE protein or hPFTAIRE mRNA. hPFTAIRE protein can be detected using hPFTAIRE-specific antibodies of the present invention. The antibodies can be labeled, for example, with a radioactive, fluorescent, biotinylated, or enzymatic tag and detected directly, or can be detected using indirect immunochemical methods, using a labeled secondary antibody. Any immunochemical method can be used to detect the presence of hPFTAIRE protein, such as immunocytochemistry, Western blots or ELISAs.

A body sample can also be assayed for the presence of hPFTAIRE mRNA. hPFTAIRE; mRNA can be detected, for example, by in situ hybridization in tissue sections or in Northern blots containing poly $A^+$ mRNA. hPFTAIRE-specific polynucleotide probes can be generated using the hPFTAIRE cDNA sequence disclosed in SEQ ID NO:1. The polynucleotide probes are preferably about 15 to 50 nucleotides in length, although they can be about 8, 10, 20, 25, 30, 35, 40, 45, 60, 75, or 100 nucleotides in length. The polynucleotide probes can be synthesized chemically or can be generated from longer hPFTAIRE subgenomic polynucleotides using restriction enzymes. The polynucleotide probes can be labeled, for example, with a radioactive, biotinylated, or fluorescent tag, as is known in the art.

The body sample which is assayed can be normal or can be diseased. In a preferred embodiment, the body sample is a primary tumor or a metastatic lesion. Metastatic lesions originating from tumors of the brain, kidney, liver, lung, pancreas, heart, ovary, testis, and spleen may be identified using this method. Other tissues can also be tested for the presence or absence of hPFTAIRE protein or mRNA. Presence of an hPFTAIRE protein or mRNA in the body sample indicates that the sample comprises migrating cells.

The invention also provides compositions and methods for altering the spatial or temporal pattern of division of a human cell. hPFTAIRE expression is required for a cell to undergo a transition from the $G_2$ to M phase of the cell cycle. Mitosis at a desired time or in a particular population of cells can therefore be reduced or prevented by decreasing expression of a hPFTAIRE gene. Decreased hPFTAIRE gene expression can also be used to treat conditions characterized by high rates of mitosis, such as neoplasia, metastasis of neoplasms, and dysplastic and hyperplastic disorders. Increased hPFTAIRE gene expression can be used to treat conditions in which high rates of mitosis are desired, for example in the treatment of nerve injuries. In addition, cells which have been transiently transfected with an hPFTAIRE antisense oligonucleotide, as described below, can also be used to identify genes whose expression is dependent on an hPFTAIRE protein.

In one embodiment of the invention, expression of the hPFTAIRE gene is decreased using a ribozyme, an RNA molecule with catalytic activity. See, e.g., Cech, *Science* 236: 1532–1539; 1987; Cech, *Ann. Rev. Biochem.* 59:543–568; 1990, Cech, *Curr. Opin. Struct. Biol.* 2: 605–609; 1992, Couture and Stinchcomb, *Trends Genet.* 12: 510–515, 1996. Ribozymes can be used to inhibit gene function by cleaving an RNA sequence, as is known in the art (e.g., Haseloff et al., U.S. Pat. No. 5,641,673).

The coding sequence of an hPFTAIRE gene can be used to generate ribozymes which will specifically bind to mRNA transcribed from the hPFTAIRE gene. Methods of designing and constructing ribozymes which can cleave other RNA molecules in trans in a highly sequence specific manner have been developed and described in the art (see Haseloff et al. *Nature* 334:585–591, 1988). For example, the cleavage activity of ribozymes can be targeted to specific hPFTAIRE RNAs by engineering a discrete "hybridization" region into the ribozyme. The hybridization region contains a sequence complementary to the target hPFTAIRE RNA and thus specifically hybridizes with the target (see, for example, Gerlach et al., EP 321,201). The nucleotide sequence shown in SEQ ID NO:1 provides a source of suitable hybridization region sequences. Longer complementary sequences can be used to increase the affinity of the hybridization sequence for the target. The hybridizing and cleavage regions of the hPFTAIRE ribozyme can be integrally related; thus, upon hybridizing to the target hPFTAIRE RNA through the complementary regions, the catalytic region of the ribozyme can cleave the target.

hPFTAIRE ribozymes can be introduced into cells as part of a construct, as is known in the art and described above. Mechanical methods, such as microinjection, liposome-mediated transfection, electroporation, or calcium phosphate precipitation, can be used to introduce the ribozyme-containing construct into cells in which it is desired to decrease hPFTAIRE expression, as described above. Alternatively, if it is desired that the cells stably retain the construct, it can be supplied on a plasmid and maintained as a separate element or integrated into the genome of the cells, as is known in the art. The construct can include transcriptional regulatory elements, such as a promoter element, an enhancer or UAS element, and a transcriptional terminator signal, for controlling transcription of hPFTAIRE ribozymes in the cells.

In another embodiment of the invention, the level of hPFTAIRE protein is decreased using an antisense oligonucleotide sequence. The antisense sequence is complementary to at least a portion of the sequence encoding hPFTAIRE selected from the nucleotide sequence shown in SEQ ID NO:1. Preferably, the antisense oligonucleotide sequence is at least 11 nucleotides in length, but can be at least 12, 15, 20, 25, 30, 35, 40, 45, or 50 or more nucleotides long. Longer sequences can also be used. hPFTAIRE antisense oligonucleotide molecules can be provided in a construct and introduced into cells as disclosed herein to decrease the level of hPFTAIRE in the cells.

hPFTAIRE antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20:1–8, 1994; Sonveaux, *Meth. Mol. Biol.* 26:1–72, 1994; Uhlmann et al., *Chem. Rev.* 90:543–583, 1990.

Although precise complementarity is not required for successful duplex formation between an hPFTAIRE antisense molecule and the complementary coding sequence of an hPFTAIRE gene, antisense molecules with no more than one mismatch are preferred. One skilled in the art can easily use the calculated melting point of an hPFTAIRE antisense-sense pair to determine the degree of mismatching which will be tolerated between a particular antisense oligonucleotide and a particular hPFTAIRE coding sequence.

hPFTAIRE antisense oligonucleotides can be modified without affecting their ability to hybridize to an hPFTAIRE coding sequence. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, qr a 3', 5'-substituted oligonucleotide in which the 3' hydroxyl group or the 5' phosphate group are substituted, can also be employed in a modified antisense oligonucleotide. These modified oligonucleotides can be prepared by methods well known in the art. See, e.g., Agrawal et al., *Trends Biotechnol.* 10:152–158, 1992; Uhlmann et al., *Chem. Rev.* 90:543–584, 1990; Uhlmann et al., *Tetrahedron. Lett.* 215:3539–3542, 1987.

Antibodies of the invention which specifically bind to hPFTAIRE, particularly single-chain antibodies, can also be used to alter levels of hPFTAIRE protein. The antibodies bind to hPFTAIRE and decrease the level of hPFTAIRE protein in a cell. Polynucleotides encoding single-chain antibodies of the invention can be introduced into cells as described above.

Preferably, the mechanism used to decrease the level of hPFTAIRE in a cell decreases the level of hPFTAIRE protein or kinase activity by at least 50%, 60%, 70%, or 80%. Most preferably, the level of hPFTAIRE protein or kinase activity is decreased by at least 90%, 95%, 99%, or 100%. The effectiveness of the mechanism chosen to decrease the level of hPFTAIRE protein or kinase activity can be assessed using methods well known in the art, such as hybridization of nucleotide probes to hPFTAIRE mRNA, quantitative RT-PCR, detection of hPFTAIRE protein using hPFTAIRE-specific antibodies of the invention, or measurement of cyclin-dependent kinase activity. Assays for cyclin-dependent kinase activity are taught, for example, in Lock et al., 1997, *Cancer Chemother. Pharmacol.* 39:399–409.

Compositions comprising hPFTAIRE antibodies, ribozymes, or antisense oligonucleotides can optionally comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in hPFTAIRE compositions, for example, mineral salts such as hydrochlorides, hydrobromides, phosphates, or sulfates, as well as salts of organic acids such as acetates, proprionates, malonates, or benzoates. hPFTAIRE compositions can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for an hPFTAIRE composition.

Typically, an hPFTAIRE composition is prepared as an injectable, either as a liquid solution or suspension; however, solid forms suitable for solution or suspension in liquid vehicles prior to injection can also be prepared. An hPFTAIRE composition can also be formulated into an enteric coated tablet or gel capsule according to known methods in the art, such as those described in U.S. Pat. No. 4,853,230, EP 225,189, AU 9,224,296, and AU 9,230,801.

Administration of hPFTAIRE compositions of the invention can include local or systemic administration, including injection, oral administration, particle gun, or catheterized administration, and topical administration. Various methods can be used to administer an hPFTAIRE composition directly to a specific site in the body. For inducing apoptosis in a tumor, for example, an appropriate hPFTAIRE composition injected several times in several different locations within the body of the tumor. Alternatively, arteries which serve the tumor can be identified, and an hPFTAIRE composition can be injected into such an artery in order to deliver the composition to the tumor.

A tumor which has a necrotic center can be aspirated, and an hPFTAIRE composition can be injected directly into the now empty center of the tumor. An hPFTAIRE composition can also be administered directly to the surface of a tumor, for example, by topical application of the composition. X-ray imaging can be used to assist in certain of these delivery methods. Combination therapeutic agents, including an hPFTAIRE-specific antibody, ribozyme, or oligonucleotide or a subgenomic hPFTAIRE polynucleotide encoding an hPFTAIRE-specific antibody, ribozyme, or oligonucleotide, can be administered simultaneously or sequentially together with other therapeutic agents.

hPFTAIRE compositions can be delivered to specific tissues using receptor-mediated targeted delivery. Receptor-mediated DNA delivery techniques are taught in, for example, Findeis et al. *Trends in Biotechnol.* 11, 202–05 (1993); Chiou et al., GENE THERAPEOTCS: METHODS AND APPLICATIONS OF DIRECT GENE TRANSER, J. A. Wolff, ed., 1994; Wu & Wu, *J. Biol. Chem.* 263, 621–24, 1988; Wu et al., *J. Biol. Chem.* 269, 54246, 1994; Zenke et al., *Proc. Natl. Acad. Sci. U.S.A.* 87, 3655–59, 1990; Wu et al., *J. Biol. Chem.* 266, 338–42, 1991.

Both the dose of a particular hPFTAIRE composition and the means of administering the composition can be determined based on specific qualities of the hPFTAIRE composition, the condition, age, and weight of the patient, the progression of the particular disease being treated, and other relevant factors. If the composition contains hPFTAIRE antibodies, effective dosages of the composition are in the range of about 5 µg to about 50 µg/kg of patient body weight, about 50 µg to about 5 mg/kg, about 100 µg to about 500 µg/kg of patient body weight, and about 200 to about 250 µg/kg.

Compositions containing hPFTAIRE subgenomic polynucleotides, including antisense oligonucleotides and ribozyme-or antibody-encoding sequences, can be administered in a range of about 100 ng to about 200 mg of DNA for local administration. Suitable concentrations range from about 500 ng to about 50 mg, about 1 µg to about 2 mg, about 5 µg to about 500 µg, and about 20 µg to about 100 µg of DNA. Factors such as method of action and efficacy of transformation and expression are considerations which will affect the dosage required for ultimate efficacy of the hPFTAIRE composition. If greater expression is desired over a larger area of tissue, larger amounts of an hPFTAIRE composition or the same amount administered successively, or several administrations to different adjacent or close tissue portions of, for example, a tumor site, may be required to effect a positive therapeutic outcome. In all cases, routine experimentation in clinical trials will determine specific ranges for optimal therapeutic effect.

Expression of an endogenous hPFTAIRE gene in a cell, such as a neoplastic cell, can be altered by introducing in frame with the endogenous hPFTAIRE gene a DNA construct comprising an hPFTAIRE targeting sequence, a regulatory sequence, an exon, and an unpaired splice donor site by homologous recombination, such that a homologously recombinant cell comprising a new hPFTAIRE transcription unit is formed. The new transcription unit can be used to turn the hPFTAIRE gene on or off as desired. This method of affecting endogenous gene expression is taught in U.S. Pat. No. 5,641,670.

The targeting sequence is a segment of at least 10, 12, 15, 20, or 50 contiguous nucleotides selected from the nucleotide sequence shown in SEQ ID NO:1. The transcription unit is located upstream of a coding sequence of the endogenous hPFTAIRE gene. The exogenous regulatory sequence directs transcription of the coding sequence of the hPFTAIRE gene.

The invention also provides a method of diagnosing or prognosing neoplasia in a mammal, preferably a human. Expression of an hPFTARE gene in a first tissue suspected of being neoplastic can be compared with expression of an hPFTAIRE gene in a second tissue which is normal. Comparisons can be made, for example, by measuring levels of hPFTAIRE mRNA or hPFTAIRE protein in the first and second tissues, as is known in the art. The first and second tissues can originate from the same subject or from different subjects. The first and second tissues can be of different types, but are preferably from the same type of tissue, such as an intestinal polyp. Alternatively, standard curves of hPFTAIRE gene expression can be determined from a number of normal tissue samples and used for comparison with hPFTAIRE gene expression in a tissue suspected of being neoplastic.

Over-expression of the hPFTAIRE gene in the first tissue compared with hPFTAIRE gene expression in the second tissue or the standard curve indicates neoplasia in the first tissue. Levels of over-expression can correlate with stages of neoplasia and can be used, for example, to monitor treatment of a patient, preferably a human patient.

An hPFTAIRE subgenomic polynucleotide can also be delivered to subjects for the purpose of screening test compounds for those which are useful for enhancing transfer of hPFTAIRE subgenomic polynucleotides to the cell or for enhancing subsequent biological effects of hPFTAIRE subgenomic polynucleotides within the cell. Such biological effects include hybridization to complementary hPFTAIRE mRNA and inhibition of its translation, expression of an hPFTAIRE subgenomic polynucleotide to form an hPFTAIRE mRNA, single-chain antibody, ribozyme, oligonucleotide, or protein and/or replication and integration of an hPFTAIRE subgenomic polynucleotide. The subject can be a cell culture or an animal, preferably a mammal, more preferably a human.

Test compounds which can be screened include any substances, whether natural products or synthetic, which can be administered to the subject in vitro or in vivo. Libraries or mixtures of test compounds can be tested. The test compound can be a pharmacologic agent already known in the art or can be a compound previously unknown to have any pharmacological activity. The test compound can be naturally occurring or designed in the laboratory. It can be isolated from microorganisms, animals, or plants, and can be produced recombinantly, or synthesized by chemical methods known in the art. Test compounds or substances can be delivered before, after, or concomitantly with an hPFTAIRE subgenomic polynucleotide. They can be administered separately or in admixture with an hPFTAIRE subgenomic polynucleotide.

Integration of a delivered hPFTAIRE subgenomic polynucleotide can be monitored by any means known in the art. For example, Southern blotting of the delivered hPFTAIRE subgenomic polynucleotide can be performed. A change in the size of the fragments of a delivered polynucleotide indicates integration. Replication of a delivered polynucleotide can be monitored inter alia by detecting incorporation Over-expression of the hPFTAIRE gene in the first tissue compared with hPFTAIRE gene expression in the second tissue or the standard curve indicates neoplasia in the first tissue. Levels of over-expression can correlate with stages of neoplasia and can be used, for example, to monitor treatment of a patient, preferably a human patient.

An hPFTAIRE subgenomic polynucleotide can also be delivered to subjects for the purpose of screening test compounds for those which are useful for enhancing transfer of hPFTAIRE subgenomic polynucleotides to the cell or for enhancing subsequent biological effects of hPFTAIRE subgenomic polynucleotides within the cell. Such biological effects include hybridization to complementary hPFTAIRE mRNA and inhibition of its translation, expression of an hPFTAIRE subgenomic polynucleotide to form an hPFTAIRE mRNA, single-chain antibody, ribozyme, oligonucleotide, or protein and/or replication and integration of an hPFTAIRE subgenomic polynucleotide. The subject can be a cell culture or an animal, preferably a mammal, more preferably a human.

Test compounds which can be screened include any substances, whether natural products or synthetic, which can be administered to the subject in vitro or in vivo. Libraries or mixues of test compounds can be tested. The test compound can be a pharmacologic agent already known in the art or can be a compound previously unknown to have any pharmacological activity. The test compound can be naturally occurring or designed in the laboratory. It can be isolated from microorganisms, animals, or plants, and can be produced recombinantly, or synthesized by chemical methods known in the art. Test compounds or substances can be delivered before, after, or concomitantly with an hPFTAIRE subgenomic polynucleotide. They can be administered separately or in admixture with an hPFTAIRE subgenomic polynucleotide.

Integration of a delivered hPFTAIRE subgenomic polynucleotide can be monitored by any means known in the art. For example, Southern blotting of the delivered hPFTAIRE subgenomic polynucleotide can be performed. A change in the size of the fragments of a delivered polynucleotide indicates integration. Replication of a delivered polynucleotide can be monitored inter alia by detecting incorporation of labeled nucleotides combined with hybridization to an hPFTAIRE probe. Expression of an hPFTAIRE subgenomic polynucleotide can be monitored by detecting production of hPFTAIRE mRNA which hybridizes to the delivered polynucleotide or by detecting hPFTAIRE protein. hPFTAIRE protein can be detected immunologically. Thus, the delivery of hPFTAIRE subgenomic polynucleotides according to the present invention provides an excellent system for screening test compounds for their ability to enhance transfer of hPFTAIRE polynucleotides to a cell, by enhancing delivery, integration, hybridization, expression, replication or integration in a cell in vitro or in vivo in an animal, preferably a mammal, more preferably a human.

In another embodiment of the invention, mitosis can be induced, increased, or promoted by increasing expression of an hPFTAIRE gene. Increasing hPFTAIRE gene expression is useful, for example, for increasing the number of cells in a cell population in vitro or for treating disorders, such as anemia, which are characterized by lowered rates of mitosis.

A composition comprising all or a portion of an hPFTAIRE gene or expression product can be introduced into a cell. The entire hPFTAIRE coding sequence or protein can be introduced, as described above. Alternatively, a portion of the hPFTAIRE protein which promotes mitosis can be identified and that portion or a nucleotide sequence encoding it can be introduced into the cell. Portions of hPFTAIRE protein which promote mitosis can be identified by introducing expression constructs which express different portions of the protein into cells and measuring alterations in the rate of mitosis. Rates of mitosis can be measured, for example, by detecting incorporation of labeled nucleotides, as is known in the art.

The invention also provides a means of screening test compounds for the ability to induce or prevent mitosis. A cell is contacted with a test compound. The cell can be any primary human cell or human cell line which expresses an hPFTAIRE gene, as disclosed above. Methods of establishing cultures of primary human cells or of culturing cell lines are well known in the art.

Expression of the hPFTAIRE gene is detected. Means of detecting hPFTAIRE gene expression, for example, by detecting hPFTAIRE mRNA or hPFTAIRE protein, are disclosed above. Expression can be measured in a sample of the same cell population before and after contact with the test compound. Alternatively, control cell populations can be employed. A test compound which increases expression of the hPFTAIRE gene is identified as a potential agent for inducing mitosis. A test compound which decreases expression of the hPFTAIRE gene is identified as a potential agent for decreasing mitosis.

The invention provides knock-out mammals whose endogenous hPFTAIRE gene is not expressed. Methods of making knock-out mammals are well known in the art. The mammal can be any experimental mammal, such as a mouse, rat, or rabbit; however, a mouse is preferred. The endogenous wild-type hPFTAIRE gene of the mammal can be deleted entirely, resulting in an absence of hPFTAIRE protein in the mammal. Alternatively, mutations such as deletions, insertions, missense substitutions, or inversions, can be introduced into the hPFTAIRE gene. Such mutations result in expression of truncated or otherwise aberrant forms of hPFTAIRE protein in the knock-out mammal. Mammalian cell lines which do not express an endogenous hPFTAIRE gene can also be constructed, as is known in the art.

Knock-out mammals and cells of the invention are useful as model systems for studying the effects of drugs in the absence of wild-type hPFTAIRE protein or in the presence of altered forms of the hPFTAIRE protein in the mammal or cell. Knock-out mammals can also be used to develop therapeutic treatments for diseases associated with alterations in hPFTAIRE gene expression, such as neoplasia.

The complete contents of all references cited in this disclosure are expressly incorporated herein by reference.

What is claimed is:

1. A cDNA molecule which comprises SEQ ID NO:1.

2. A construct comprising:
   a promoter; and
   a polynucleotide encoding an hPFTAIRE protein having an amino acid sequence as shown in SEQ ID NO:2, wherein said polynucleotide is located downstream from the promoter, wherein transcription of said polynucleotide initiates at the promoter, arid wherein said polynucleotide comprises the nucleotide sequence shown in SEQ ID NO:1.

3. A host cell comprising a construct which comprises:
   a promoter; and
   a polynucleotide encoding an hPFTAIRE protein having the amino acid sequence as shown in SEQ ID NO:2, wherein said polynucleotide comprises the nucleotide sequence shown in SEQ ID NO:1.

4. A cDNA molecule which is at least 95% identical to the nucleotide sequence shown in SEQ ID NO:1, wherein said cDNA molecule encodes an hPFTAIRE protein having the amino acid sequence as shown in SEQ ID NO:2, and wherein said protein has cyclin-dependent kinase activity.

5. The cDNA molecule of cDNA of claim 4 which is at least 96% identical to the nucleotide sequence shown in SEQ 1D NO:1, wherein said cDNA molecule encodes an hPFTAIRE protein having the amino acid sequence as shown in SEQ ID NO:2, and wherein said protein has cyclin-dependent kinase activity.

6. The cDNA molecule of claim 4 which is at least 97% identical to the nucleotide sequence shown in SEQ ID NO:1, wherein said cDNA molecule encodes an hPFTAIRE protein having the amino acid sequence as shown in SEQ ID NO:2, and wherein said protein has cyclin-dependent kinase activity.

7. The cDNA molecule of claim 4 which is at least 98% identical to the nucleotide sequence shown in SEQ ID NO:1, wherein said cDNA molecule encodes an hPFTAIRE protein having the amino acid sequence as shown in SEQ ID NO:2, and wherein said protein has cyclin-dependent kinase activity.

8. The cDNA molecule of claim 4 which is at least 99% identical to the nucleotide sequence shown in SEQ ID NO:1, wherein said cDNA molecule encodes an hPFTAIRE protein having the amino acid sequence as shown in SEQ ID NO:2, and wherein said protein has cyclin-dependent kinase activity.

* * * * *

SEQUENCE LISTING

```
<160> NUMBER OF SEQ ID NOS:   13

<210> SEQ ID NO 1
<211> LENGTH: 1272
<212> TYPE: DNA
<213> ORGANISM: human

<400> SEQUENCE: 1
atgtctacac ggaactgcca gggaatggac tcagtgatca aaccectgga cacaattcct        60 gaggataaaa aagtcagagt tcagaggaca cagagcactt ttgacccatt tgagaaacca       120
gctaatcaag taaagagggt gcattctgag aacaatgctt gcattaactt taagacctcc       180
tccactggca aagagtcacc taaagttagg cggcactcca gccccagctc gccaacaagt       240
cccaaatttg gaaaagctga ctcatatgaa aagctggaaa aactagggga aggatcttat       300
gctacagtat acaaagggaa aagcagggta aatgggaagt tggtagctct gaaggtgatc       360
aggctgcagg aagaagaagg gacacctttc acagctatca gggaagcttc tcttttaaaa       420
ggactaaaac atgctaacat agtgctactt catgacatca tccataccaa ggagacgctg       480
acacttgtgt ttgaatatgt gcacactgat ttatgtcagt acatggacaa gcaccctggg       540
gggctgcatc cagataatgt gaagttgttt ttatttcagt tgctgcgagg tctgtcttac       600
atccaccagc gttatatttt gcacagagac ctgaaaccac agaaccttct gatcagtgac       660
acgggggagt taaagctggc agatttcggt cttgcaagag caaaatccgt ccctagccac       720
acatactcca acgaagtggt taccttgtgg tacagacctc cagatgtcct tctaggctca       780
acagaatatt ccacctgcct tgacatgtgg ggagtaggtt gcatctttgt tgaaatgatc       840
caaggagttg ctgcttttcc aggaatgaaa gacattcagg atcaacttga acgaatattt       900
ctggttcttg gaacaccaaa tgaggacaca tggcctggag ttcattcttt accacatttt       960
aagccagaac gctttaccct gtacagctct aaaaaccttta gacaagcatg gaataagctc      1020
agctatgtga accatgcaga ggacctggcc tccaagctcc tacaatgttc cccaaagaac      1080
agactgtcgg cacaggctgc cttgagccac gagtatttta gtgacctgcc gccacggcta      1140
tgggaactca ccgacatgtc ttctattttt actgtcccaa atgtgagatt gcaaccagaa      1200
gctggagaaa gcatgcgggc ctttgggaaa aacaatagtt atggcaaaag tctatcaaac      1260
agcaagcact ga                                                          1272

<210> SEQ ID NO 2
<211> LENGTH: 423
<212> TYPE: PRT
<213> ORGANISM: Homo sapiens

<400> SEQUENCE: 2

Met Ser Thr Arg Asn Cys Gln Gly Met Asp Ser Val Ile Lys Pro Leu
  1               5                  10                  15
```

-continued

```
Asp Thr Ile Pro Glu Asp Lys Lys Val Arg Val Gln Arg Thr Gln Ser
             20                  25                  30
Thr Phe Asp Pro Phe Glu Lys Pro Ala Asn Gln Val Lys Arg Val His
         35                  40                  45
Ser Glu Asn Asn Ala Cys Ile Asn Phe Lys Thr Ser Ser Thr Gly Lys
 50                  55                  60
Glu Ser Pro Lys Val Arg Arg His Ser Ser Pro Ser Ser Pro Thr Ser
 65                  70                  75                  80
Pro Lys Phe Gly Lys Ala Asp Ser Tyr Glu Lys Leu Glu Lys Leu Gly
                 85                  90                  95
Glu Gly Ser Tyr Ala Thr Val Tyr Lys Gly Lys Ser Arg Val Asn Gly
            100                 105                 110
Lys Leu Val Ala Leu Lys Val Ile Arg Leu Gln Glu Glu Glu Gly Thr
            115                 120                 125
Pro Phe Thr Ala Ile Arg Glu Ala Ser Leu Leu Lys Gly Leu Lys His
            130                 135                 140
Ala Asn Ile Val Leu Leu His Asp Ile Ile His Thr Lys Glu Thr Leu
145                 150                 155                 160
Thr Leu Val Phe Glu Tyr Val His Thr Asp Leu Cys Gln Tyr Met Asp
                165                 170                 175
Lys His Pro Gly Gly Leu His Pro Asp Asn Val Lys Leu Phe Leu Phe
            180                 185                 190
Gln Leu Leu Arg Gly Leu Ser Tyr Ile His Gln Arg Tyr Ile Leu His
            195                 200                 205
Arg Asp Leu Lys Pro Gln Asn Leu Leu Ile Ser Asp Thr Gly Glu Leu
            210                 215                 220
Lys Leu Ala Asp Phe Gly Leu Ala Arg Ala Lys Ser Val Pro Ser His
225                 230                 235                 240
Thr Tyr Ser Asn Glu Val Val Thr Leu Trp Tyr Arg Pro Pro Asp Val
                245                 250                 255
Leu Leu Gly Ser Thr Glu Tyr Ser Thr Cys Leu Asp Met Trp Gly Val
            260                 265                 270
Gly Cys Ile Phe Val Glu Met Ile Gln Gly Val Ala Ala Phe Pro Gly
            275                 280                 285
Met Lys Asp Ile Gln Asp Gln Leu Glu Arg Ile Phe Leu Val Leu Gly
            290                 295                 300
Thr Pro Asn Glu Asp Thr Trp Pro Gly Val His Ser Leu Pro His Phe
305                 310                 315                 320
Lys Pro Glu Arg Phe Thr Leu Tyr Ser Ser Lys Asn Leu Arg Gln Ala
                325                 330                 335
Trp Asn Lys Leu Ser Tyr Val Asn His Ala Glu Asp Leu Ala Ser Lys
            340                 345                 350
Leu Leu Gln Cys Ser Pro Lys Asn Arg Leu Ser Ala Gln Ala Ala Leu
            355                 360                 365
Ser His Glu Tyr Phe Ser Asp Leu Pro Pro Arg Leu Trp Glu Leu Thr
            370                 375                 380
Asp Met Ser Ser Ile Phe Thr Val Pro Asn Val Arg Leu Gln Pro Glu
385                 390                 395                 400
Ala Gly Glu Ser Met Arg Ala Phe Gly Lys Asn Asn Ser Tyr Gly Lys
                405                 410                 415
Ser Leu Ser Asn Ser Lys His
            420
```

<210> SEQ ID NO 3
<211> LENGTH: 2467
<212> TYPE: DNA
<213> ORGANISM: mouse

<400> SEQUENCE: 3

| | | | | | |
|---|---|---|---|---|---|
| gaattcagtt | gctgtctgag | gctggcttgg | tgcaaacaca | ttgctagaga | tatgttaagg | 60 |
| agttccaggt | gaatccggct | caagagagac | aacagcataa | acgatatgtg | tcacaaagat | 120 |
| gtctacccgg | aactgccagg | ggacagattc | agtgatcaag | cacctggaca | caattcctga | 180 |
| agacaagaaa | gtcagggttc | agaggacgca | gagcactttt | gacccatttg | agaaaccagc | 240 |
| caaccaagtc | aaaagggtcc | attctgagaa | caatgcatgc | attaacttta | aatcctcctc | 300 |
| tgctggcaaa | gagtcaccta | aagttcggcg | gcactccagc | cccagctcgc | caacgagtcc | 360 |
| caaatttgga | aaagctgact | catacgaaaa | actggaaaaa | ctgggggaag | gatcttatgc | 420 |
| aacagtgtac | aaagggaaaa | gcaaagtgaa | tgggaagctg | gtggctctaa | aggtgatccg | 480 |
| gctgcaggaa | gaagagggca | cacctttcac | agccatcagg | gaagcttccc | tgttgaaagg | 540 |
| actaaagcac | gccaacatcg | tgttgcttca | cgacatcatc | cacactaagg | aaaccctgac | 600 |
| ccttgtcttt | gaatacgtgc | acactgattt | atgtcagtac | atggacaagc | acctggagg | 660 |
| actccatcca | gataatgtga | agttgttttt | atttcagctg | ctgcgaggac | tgtcttacat | 720 |
| ccaccagcgt | tatattttgc | acagagacct | gaaaccgcag | aaccttctca | tcagcgatac | 780 |
| gggggagttg | aagctggcag | atttcggtct | ggcaagagca | aaatccgtcc | ctagccacac | 840 |
| atactccaat | gaagtggtta | ccttgtggta | cagacctcca | gatgttcttc | tgggctctac | 900 |
| agaatattcc | acctgccttg | acatgtgggg | agttggctgt | atcttcgttg | agatgatcca | 960 |
| aggagttgct | gcgtttccag | gaatgaaaga | cattcaggat | caacttgaac | ggatatttct | 1020 |
| ggttcttgga | acaccgaatg | aggacacgtg | gcctggagtt | cattctttac | acatttttaa | 1080 |
| gccagaacgc | tttaccgtgt | acaactctaa | aagccttaga | caagcatgga | ataagctcag | 1140 |
| ctatgtaaat | catgctgaag | acttggcctc | caagcttctc | cagtgttccc | caaagaacag | 1200 |
| gctatcagca | caggccgcct | tgagccatga | gtatttcagc | gatctgcctc | cacggctatg | 1260 |
| ggagctgact | gatatgtctt | ctattttttac | cgtcccaaat | gtgagattgc | aaccagaagc | 1320 |
| tggagagagc | atgagggcct | ttggaaaaaa | caatagttat | gggaaaagcc | tatcgaacag | 1380 |
| caaaacactga | caagcccggc | actctcagga | gagcacagga | ttaagttgtc | atcattctgg | 1440 |
| gaagaagaag | aagagataaa | aataaatcaa | tcaataaaaa | ccactaatga | agtggctcag | 1500 |
| tgcgagggcc | ctgaatcggt | tctcttctgc | ccggtgcagt | ggatttcact | gacatgaaaa | 1560 |
| tggaagctgg | caagaacctg | tttcctctgc | aatttattta | aaaccttgca | cgcatttgga | 1620 |
| taccttgtga | cttccaagaa | ctacgtgacg | attaagcttg | gcatgtattc | ttttccgtct | 1680 |
| tttgtgtctg | gttctgttg | cttccccctg | ccgcacagtg | tccatcgcac | ggtgtctctg | 1740 |
| tgaagggttt | tgctgctttc | agccagctcc | tcttaagtac | attaagacaa | cacatttggt | 1800 |
| gttcacactt | cctcagccat | gtctgcactt | gaaagccaca | cagcggcagg | agacaatgtg | 1860 |
| tgatttccct | gagagcagag | tgcattctgc | aacctccagg | aagaacattc | ttttttgctaa | 1920 |
| aacaaactcc | atgctttctg | acagactaga | cagcgtggtc | ccagacagtg | gggccctacc | 1980 |
| tgttgcctgc | cttggaggac | atttagaaat | gtaagggttt | ttttgttttg | ttttggtttt | 2040 |
| cgtttttttat | gtgaaagtag | cacacattta | cacaggagac | caaaatccac | ttgctatttc | 2100 |
| aatagcctga | ctgtttctga | gcaggtagag | aaataaacat | ggaaaacaaa | gacagggtga | 2160 |

```
ctgaaggtta ataagcatta ctatcatttt ttttagcctg tagaaagcaa ggcaactttt      2220
tcatgtgctc ttgtccacat cttaccttttt cccatcagct ctgtattatt aaactgttac      2280
actctatttt taaactggag aaaatagtag caaatatcat tcttaaaacc tgggtacata      2340
gaaaaaaaaa tctgtctgtc agggtaggtc ctgaatgcag ccttggctga ttaaagctta      2400
gaaatcacat tttaaaatta tccagagtta aaaatgagct tatttacgac aaaggacctt      2460
tgaattc                                                                2467

<210> SEQ ID NO 4
<211> LENGTH: 423
<212> TYPE: PRT
<213> ORGANISM: mouse

<400> SEQUENCE: 4
```

| Met | Ser | Thr | Arg | Asn | Cys | Gln | Gly | Thr | Asp | Ser | Val | Ile | Lys | His | Leu |
|---|---|---|---|---|---|---|---|---|---|---|---|---|---|---|---|
| 1 | | | | 5 | | | | | 10 | | | | | 15 | |

Asp Thr Ile Pro Glu Asp Lys Lys Val Arg Val Gln Arg Thr Gln Ser
              20                  25                  30

Thr Phe Asp Pro Phe Glu Lys Pro Ala Asn Gln Val Lys Arg Val His
          35                  40                  45

Ser Glu Asn Asn Ala Cys Ile Asn Phe Lys Ser Ser Ala Gly Lys
    50                  55                  60

Glu Ser Pro Lys Val Arg Arg His Ser Ser Pro Ser Pro Thr Ser
65                  70                  75                  80

Pro Lys Phe Gly Lys Ala Asp Ser Tyr Glu Lys Leu Glu Lys Leu Gly
                85                  90                  95

Glu Gly Ser Tyr Ala Thr Val Tyr Lys Gly Lys Ser Lys Val Asn Gly
            100                 105                 110

Lys Leu Val Ala Leu Lys Val Ile Arg Leu Gln Glu Glu Glu Gly Thr
        115                 120                 125

Pro Phe Thr Ala Ile Arg Glu Ala Ser Leu Leu Lys Gly Leu Lys His
    130                 135                 140

Ala Asn Ile Val Leu Leu His Asp Ile Ile His Thr Lys Glu Thr Leu
145                 150                 155                 160

Thr Leu Val Phe Glu Tyr Val His Thr Asp Leu Cys Gln Tyr Met Asp
                165                 170                 175

Lys His Pro Gly Gly Leu His Pro Asp Asn Val Lys Leu Phe Leu Phe
            180                 185                 190

Gln Leu Leu Arg Gly Leu Ser Tyr Ile His Gln Arg Tyr Ile Leu His
        195                 200                 205

Arg Asp Leu Lys Pro Gln Asn Leu Leu Ile Ser Asp Thr Gly Glu Leu
    210                 215                 220

Lys Leu Ala Asp Phe Gly Leu Ala Arg Ala Lys Ser Val Pro Ser His
225                 230                 235                 240

Thr Tyr Ser Asn Glu Val Val Thr Leu Trp Tyr Arg Pro Pro Asp Val
                245                 250                 255

Leu Leu Gly Ser Thr Glu Tyr Ser Thr Cys Leu Asp Met Trp Gly Val
            260                 265                 270

Gly Cys Ile Phe Val Glu Met Ile Gln Gly Val Ala Ala Phe Pro Gly
        275                 280                 285

Met Lys Asp Ile Gln Asp Gln Leu Glu Arg Ile Phe Leu Val Leu Gly
    290                 295                 300

Thr Pro Asn Glu Asp Thr Trp Pro Gly Val His Ser Leu Pro His Phe
305                 310                 315                 320

-continued

```
Lys Pro Glu Arg Phe Thr Val Tyr Asn Ser Lys Ser Leu Arg Gln Ala
                325                 330                 335

Trp Asn Lys Leu Ser Tyr Val Asn His Ala Glu Asp Leu Ala Ser Lys
            340                 345                 350

Leu Leu Gln Cys Ser Pro Lys Asn Arg Leu Ser Ala Gln Ala Ala Leu
        355                 360                 365

Ser His Glu Tyr Phe Ser Asp Leu Pro Pro Arg Leu Trp Glu Leu Thr
    370                 375                 380

Asp Met Ser Ser Ile Phe Thr Val Pro Asn Val Arg Leu Gln Pro Glu
385                 390                 395                 400

Ala Gly Glu Ser Met Arg Ala Phe Gly Lys Asn Asn Ser Tyr Gly Lys
                405                 410                 415

Ser Leu Ser Asn Ser Lys His
            420

<210> SEQ ID NO 5
<211> LENGTH: 7
<212> TYPE: PRT
<213> ORGANISM: human

<400> SEQUENCE: 5

Pro Phe Thr Ala Ile Arg Glu
1               5

<210> SEQ ID NO 6
<211> LENGTH: 7
<212> TYPE: PRT
<213> ORGANISM: human

<400> SEQUENCE: 6

Asn Arg Thr Ala Leu Arg Glu
1               5

<210> SEQ ID NO 7
<211> LENGTH: 7
<212> TYPE: PRT
<213> ORGANISM: human

<400> SEQUENCE: 7

Pro Ile Ser Ser Leu Arg Glu
1               5

<210> SEQ ID NO 8
<211> LENGTH: 7
<212> TYPE: PRT
<213> ORGANISM: human

<400> SEQUENCE: 8

Pro Ile Thr Ala Leu Arg Glu
1               5

<210> SEQ ID NO 9
<211> LENGTH: 7
<212> TYPE: PRT
<213> ORGANISM: human

<400> SEQUENCE: 9

Pro Leu Ser Thr Ile Arg Glu
1               5

<210> SEQ ID NO 10
<211> LENGTH: 7
```

```
<212> TYPE: PRT
<213> ORGANISM: human

<400> SEQUENCE: 10

Pro Ile Ser Thr Val Arg Glu
 1               5

<210> SEQ ID NO 11
<211> LENGTH: 7
<212> TYPE: PRT
<213> ORGANISM: human

<400> SEQUENCE: 11

Pro Ser Thr Ala Ile Arg Glu
 1               5

<210> SEQ ID NO 12
<211> LENGTH: 7
<212> TYPE: PRT
<213> ORGANISM: human

<400> SEQUENCE: 12

Pro Asn Gln Ala Leu Arg Glu
 1               5

<210> SEQ ID NO 13
<211> LENGTH: 1549
<212> TYPE: DNA
<213> ORGANISM: Homo sapiens

<400> SEQUENCE: 13
ctcaagctat gcatccaacg cgttgggagc tctcccatat ggtcgacctg caggcggccg      60
cgaattcact agtgatttac ggctgcgaga agacgacaga agggggagaa gatcggcaag     120
atgaagaagt tgcggagaac tttgtcggag agtttcagtc gcattgcttt gaagaaagat     180
gacaccacct ttgatgagat atgtgtcaca agatgtctca cacggaactg ccagggaatg     240
gactcagtga tcaaacccct ggacacaatt cctgaggata aaaagtcag agttcagagg      300 acacagagca cttttgaccc atttgagaaa ccagctaatc aagtaaagag ggtgcattct     360
gagaacaatg cttgcattaa ctttaagacc tcctccactg gcaaagagtc acctaaagtt     420
aggcggcact ccagccccag ctcgccaaca agtcccaaat ttggaaaagc tgactcatat     480
gaaaagctgg aaaaactagg ggaaggatct tatgctacag tatacaaagg gaaagcagg     540 gtaaatggga agttggtagc tctgaaggtg atcaggctgc aggaagaaga agggacacct     600
ttcacagcta tcagggaagc ttctcttta aaaggactaa acatgctaa catagtgcta      660 cttcatgaca tcatccatac caaggagacg ctgacacttg tgtttgaata tgtgcacact     720
gatttatgtc agtacatgga caagcaccct gggggctgc atccagataa tgtgaagttg     780
tttttatttc agttgctgcg aggtctgtct tacatccacc agcgttatat tttgcacaga     840
gacctgaaac cacagaacct tctgatcagt gacacggggg agttaaagct ggcagatttc     900
ggtcttgcaa gagcaaaatc cgtccctagc cacacatact ccaacgaagt ggttaccttg     960
tggtacagac tccagatgt ccttctaggc tcaacagaat attccacctg ccttgacatg    1020
tggggagtag gttgcatctt tgttgaaatg atccaaggag ttgctgcttt tccaggaatg    1080
aaagacattc aggatcaact tgaacgaata tttctggttc ttggaacacc aaatgaggac    1140
acatggcctg gagttcattc tttaccactt tttaagccaa acgctttac cctgtacagc    1200 tctaaaaacc ttagacaagc atggaataag ctcagctatg tgaaccatgc agaggacctg    1260
```

-continued

```
gcctccaagc tcctacaatg ttccccaaag aacagactgt cggcacaggc tgccttgagc    1320
cacgagtatt ttagtgacct gccgccacgg ctatgggaac tcaccgacat gtcttctatt    1380
tttactgtcc caaatgtgag attgcaacca gaagctggag aaagcatgcg ggcctttggg    1440
aaaaacaata gttatggcaa aagtctatca aacagcaagc actgacaagc agcacattct    1500
caagagcaca caggattaag ttgtcatcat tctgggaaaa aaaaaaaa                 1549
```